United States Patent
Jacoby et al.

(10) Patent No.: US 12,037,341 B2
(45) Date of Patent: Jul. 16, 2024

(54) PROCESS FOR PREPARING BICYCLIC ENOLETHER

(71) Applicant: FIRMENICH SA, Satigny (CH)

(72) Inventors: Denis Jacoby, Satigny (CH); Catherine Gandara, Satigny (CH)

(73) Assignee: FIRMENICH SA, Satigny (CH)

( * ) Notice: Subject to any disclaimer, the term of this patent is extended or adjusted under 35 U.S.C. 154(b) by 618 days.

(21) Appl. No.: 17/299,405

(22) PCT Filed: Apr. 9, 2020

(86) PCT No.: PCT/EP2020/060236
§ 371 (c)(1),
(2) Date: Jun. 3, 2021

(87) PCT Pub. No.: WO2020/212264
PCT Pub. Date: Oct. 22, 2020

(65) Prior Publication Data
US 2022/0056042 A1    Feb. 24, 2022

(30) Foreign Application Priority Data
Apr. 15, 2019    (EP) .................................... 19169290

(51) Int. Cl.
*C07D 493/08*    (2006.01)
(52) U.S. Cl.
CPC .................. *C07D 493/08* (2013.01)
(58) Field of Classification Search
CPC .............................. C07D 493/08; B01J 31/24
USPC ...................................................... 549/355
See application file for complete search history.

(56) References Cited

FOREIGN PATENT DOCUMENTS

| | | |
|---|---|---|
| EP | 3199514 A1 | 8/2017 |
| EP | 3862356 A1 | 8/2021 |
| JP | 2018535982 A | 12/2018 |
| WO | 2018011386 A1 | 1/2018 |
| WO | 2019086207 A1 | 5/2019 |

OTHER PUBLICATIONS

International Search Report and Written Opinion for corresponding PCT/EP2020/060236, mailed May 29, 2020, 13 Pages.

*Primary Examiner* — Jeffrey H Murray
(74) *Attorney, Agent, or Firm* — Armstrong Teasdale LLP

(57) ABSTRACT

Described herein is a process for preparing a compound of formula (I)

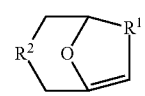

(I)

starting from a compound of formula (II)

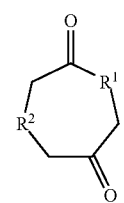

(II)

where the process is catalyzed by a metal complex.

15 Claims, No Drawings

PROCESS FOR PREPARING BICYCLIC ENOLETHER

CROSS-REFERENCE TO RELATED APPLICATIONS

This application is a U.S. National Phase Application of International Patent Application No. PCT/EP2020/060236, filed Apr. 9, 2020, which claims priority to European Patent Application No. 19169290.4, filed Apr. 15, 2019, the entire contents of which are hereby incorporated by reference herein.

TECHNICAL FIELD

The present invention relates to the field of organic synthesis and more specifically it concerns a process for preparing compound of formula (I) catalyzed by a metal complex.

BACKGROUND

The bicyclic enol ether derivative of formula (I) is typical intermediate toward more valuable compounds, such as saturated or unsaturated cyclic ketones. For examples, 16-oxabicyclo[10.3.1]hexadec-12-ene or 14-methyl-16-oxabicyclo[10.3.1]hexadec-12-ene are key intermediates toward highly appreciated perfumery ingredients such as Exaltenone or Muscenone® (trademark from Firmenich SA). Said intermediates have been obtained since decades thanks to the double reduction of a macrocyclic dione; e.g. 1,5-cyclopentadecanedione or 3-methylcyclopentadecane-1,5-dione, into the corresponding macrocyclic diol; e.g. 1,5-cyclopentadecanediol or 3-methylcyclopentadecane-1,5-diol, followed by dehydrogenation and dehydration to form a macrocyclic enol ether. The direct enol ether formation from the dione starting material has never been reported.

So, there is still a need to develop such a more straightforward approach toward bicyclic enolether while improving the yield.

The present invention allows obtaining compound of formula (I) starting from cyclic diketone of formula (II) under transfer hydrogenation conditions using a secondary alcohol as a source of hydrogen.

SUMMARY OF THE INVENTION

The invention relates to a novel process allowing the preparation of compound of formula (I) starting from compound of formula (II) while avoiding the formation and isolation step of the corresponding diol.

So, the object of the present invention is a process for the preparation of a compound of formula (I)

in a form of any one of its stereoisomers or a mixture thereof and wherein $R^1$ represents a linear or branched $C_{1-5}$ alkanediyl or alkenediyl group, optionally substituted by a phenyl group and $R^2$ represents a linear or branched $C_{1-10}$ alkanediyl or alkenediyl group, optionally substituted by a phenyl group;

comprising the reaction of a compound of the formula (II)

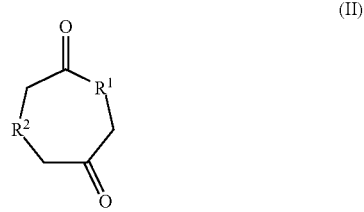

in a form of any one of its stereoisomers and wherein $R^1$ and $R^2$ have the same meaning as defined in formula (I);

with metal catalyst, provided that ruthenium catalyst is excluded, and in the presence of a hydrogen source.

DESCRIPTION OF THE INVENTION

Surprisingly, it has now been discovered that the compound of formula (I) can be produced in an advantageous manner by means of a one-pot reduction and cyclisation-dehydration type reaction of compound of formula (II) under transfer hydrogenation conditions. The invention's conditions allow avoiding the difficult handling of the corresponding diol and are highly selective toward monoreduction. The invention's process leads to the formation of a bicyclic enol ether in high yield without compromise on the conversion. In addition, the invention's process uses a catalytic system which may be recycled and circumventing the use of toxic reagent such as borohydride, rendering said transformation more sustainable.

Therefore, a first object of the present invention is process for the preparation of a compound of formula (I)

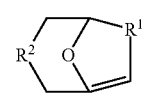

in a form of any one of its stereoisomers or a mixture thereof and wherein $R^1$ represents a linear or branched $C_{1-5}$ alkanediyl or alkenediyl group, optionally substituted by a phenyl group and $R^2$ represents a linear or branched $C_{1-10}$ alkanediyl or alkenediyl group, optionally substituted by a phenyl group;

comprising, or consisting of, the reaction of a compound of the formula (II)

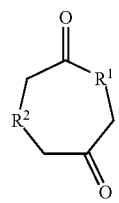

in a form of any one of its stereoisomers and wherein $R^1$ and $R^2$ have the same meaning as defined in formula (I);

with a metal catalyst, provided that ruthenium catalyst is excluded, and in the presence of a hydrogen source.

According to any embodiments of the invention, the invention process is a one step process.

According to any embodiments of the invention, the invention process is a full conversion process.

By "full conversion process", it is meant the normal meaning in the art; i.e. the invention's process is performed until complete transformation of compound of formula (II).

According to any embodiments of the invention, a compound of formula (III)

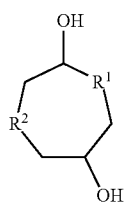

(III)

in a form of any one of its stereoisomers and wherein $R^1$ and $R^2$ have the same meaning as defined in formula (I);

is not formed.

In other words, the invention's process allows obtaining compound of formula (I) in one step without the formation of the double reduction product of formula (III). The invention's process allows obtaining mainly compound of formula (I) without the formation of the undesired over-hydrogenated diol of formula (III); i.e. the invention's process is highly selective.

According to any embodiments of the invention, and independently of the specific aspects, the compound (I) as well as the corresponding compound (II) can be in the form of any one of its stereoisomers or mixture thereof. For the sake of clarity by the term stereoisomer it is intended any diastereoisomers, enantiomers, racemate.

Indeed, the compound (I) or (II) may have at least one stereogenic center which can have different stereochemistry (i.e. when two stereogenic centers are present, compound (I) or (II) can have (R,R) or (R,S) configuration). Each of said stereogenic centers can be in a relative or absolute configuration R or S or a mixture thereof or in other words said compound of formula (II) or (I) can be in a form of pure enantiomer or diastereoisomer, or in a form of a mixture of stereoisomers.

According to any one of the above embodiments of the invention, said compounds of formula (II) are $C_7$-$C_{20}$ compounds.

According to any one of the above embodiments of the invention, compound (I) may be a compound of formula

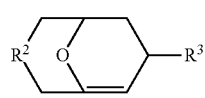

(I')

in a form of any one of its stereoisomers and wherein $R^2$ has the same meaning as defined in formula (I) and $R^3$ represents a hydrogen atom or a methyl group.

According to any one of the above embodiments of the invention, compound (II) may be a compound of formula

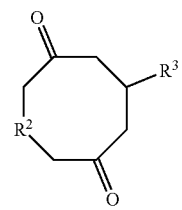

(II')

in a form of any one of its stereoisomers and wherein $R^2$ has the same meaning as defined in formula (I) and $R^3$ represents a hydrogen atom or a methyl group.

According to any embodiments of the invention, $R^1$ represents linear or branched $C_{1-5}$ alkanediyl or alkenediyl group optionally substituted by a phenyl group. Preferably, $R^1$ represents a linear or branched $C_{1-4}$ alkanediyl group. Preferably, $R^1$ represents a linear or branched $C_{2-3}$ alkanediyl group. Even more preferably, $R^1$ represents a 1,2-propanediyl group or a 1,2-ethanediyl group. Even more preferably, $R^1$ represents a 1,2-propanediyl group.

According to any embodiments of the invention, $R^2$ represents a linear or branched $C_{1-10}$ alkanediyl or alkenediyl group optionally substituted by a phenyl group. Preferably, $R^2$ represents a linear or branched $C_{1-10}$ alkanediyl group. Preferably, $R^2$ represents a linear or branched $C_{4-9}$ alkanediyl group. Preferably, $R^2$ represents a linear or branched $C_{6-9}$ alkanediyl group. Even more preferably, $R^2$ represents a 1,8-octanediyl group.

According to any embodiments of the invention, $R^3$ represents a hydrogen atom or a methyl group. Preferably, $R^3$ may represent a methyl group.

Non-limiting examples of suitable compounds of formula (I) may include 12-oxabicyclo[6.3.1]dodec-8-ene, 10-methyl-12-oxabicyclo[6.3.1]dodec-8-ene, 13-oxabicyclo[7.3.1]tridec-9-ene, 11-methyl-13-oxabicyclo[7.3.1]tridec-9-ene, 14-oxabicyclo[8.3.1]tetradec-10-ene, 12-methyl-14-oxabicyclo[8.3.1]tetradec-10-ene, 15-oxabicyclo[9.3.1]pentadec-11-ene, 13-methyl-15-oxabicyclo[9.3.1]pentadec-11-ene, 16-oxabicyclo[10.3.1]hexadec-12-ene, 14-methyl-16-oxabicyclo[10.3.1]hexadec-12-ene, 17-oxabicyclo[11.3.1]heptadec-13-ene or 15-methyl-17-oxabicyclo[11.3.1]heptadec-13-ene. Preferably, the compound of formula (I) may be 16-oxabicyclo[10.3.1]hexadec-12-ene, 14-methyl-16-oxabicyclo[10.3.1]hexadec-12-ene, 17-oxabicyclo[11.3.1]heptadec-13-ene or 15-methyl-17-oxabicyclo[11.3.1]heptadec-13-ene. Preferably, the compound of formula (I) may be 16-oxabicyclo[10.3.1]hexadec-12-ene or 14-methyl-16-oxabicyclo[10.3.1]hexadec-12-ene. Even more preferably, the compound of formula (I) may be 14-methyl-16-oxabicyclo[10.3.1]hexadec-12-ene.

Non-limiting examples of suitable compounds of formula (II) may include cycloundecane-1,5-dione, 3-methylcycloundecane-1,5-dione, cyclododecane-1,5-dione, 3-methylcyclododecane-1,5-dione, cyclotridecane-1,5-dione, 3-methylcyclotridecane-1,5-dione, cyclotetradecane-1,5-dione, 3-methylcyclotetradecane-1,5-dione, cyclopentadecane-1,5-dione, 3-methylcyclopentadecane-1,5-dione, cyclohexadecane-1,5-dione or 3-methylcyclohexadecane-1,5-dione. Preferably, the compound of formula (II) may be cyclopentadecane-1,5-dione, 3-methylcyclopentadecane-1,5-dione, cyclohexadecane-1,5-dione or 3-methylcyclohexadecane-1,5-dione. Preferably, the compound of formula (II) may be cyclopentadecane-1,5-dione or 3-methylcyclopentadecane-1,5-dione. Even more preferably, the compound of formula (II) may be 3-methylcyclopentadecane-1,5-dione.

The compound of formula (II) is commercially available compound or can be prepared by several methods, such as the one reported in *Helvetica Chimica Acta* 1967, 50, 705, or in WO2016104474 or in WO2016184948.

According to any embodiments of the invention, the catalyst is a metal catalyst. Preferably, the metal catalyst may be of formula $$[M(O)_m(X)_n] \tag{IV}$$

wherein M is a metal selected from the group consisting of transition metal or post-transition metal, m is 0, 1 or 2, X represents an anionic ligand; and n is an integer between 1 to 6.

According to any of the above embodiments of the invention, M may be a metal selected from the group consisting of metals of column IIIA (such as Al), IVA, IIIB, IVB (such as Ti or Zr), VB (such as V), VIB and VIIB of the periodic table. Preferably, the M may be selected from the group consisting of Aluminum, Titanium, Zirconium and Vanadium.

According to any of the above embodiments of the invention, n may be an integer between 1 and 4. Preferably, n may be an integer between 2 and 4. Even more preferably, n may be 3 or 4.

According to any of the above embodiments of the invention, X represents an anionic ligand. A non-limiting list of anionic ligand includes a hydrogen or halogen atom, a hydroxy, an oxy or betadiketonato group, or an alkoxy or carboxylic radical.

By the term "betadiketonato", it is meant the normal meaning in the art; i.e a group of formula $R^a(COCHCO)^-R^a$ wherein $R^a$ are, independently from each other, a $C_1$ to $C_{18}$ alkyl group and the negative charge is delocalized.

According to any of the above embodiments of the invention, in formula (III), each X represents, simultaneously or independently, a hydrogen or fluorine, chlorine, bromine or iodine atom, a hydroxy or acetylacetonate group, a $C_1$ to $C_{18}$ alkoxy radical, such as a methoxy, ethoxy or isopropoxy, sec-butoxy radical, or a $C_1$ to $C_{18}$ carboxylic radical such as a HCOO, $CH_3COO$, $CH_3CH_2COO$ or phenylCOO radical. Preferably, each X represents, simultaneously or independently, a hydroxy, methoxy, ethoxy, propoxy, butoxy, isopropoxy, or acetylacetonate radical.

Non-limiting examples of suitable metalcatalyst of formula (III) may include[$Al(OR)_3$], [$Al(OAc)_3$], [$Al(acac)_3$], [$Ti(OR)_4$], [$Ti(O)(acac)_2$], [$Zr(OR)_4$], [$Zr(acac)_4$], [$V(O)(acac)_2$], [$V(acac)_3$], [$V(O)(OR)_3$]; R being a $C_{1-6}$ alkyl group, preferably R being a $C_{1-4}$ alkyl group.

The metal catalyst can be added into the reaction medium of the invention's process in a large range of concentrations. As non-limiting examples, one can cite as metal concentration values those ranging from 1000 ppm to 100000 ppm, relative to the total amount of substrate. Preferably, the metal concentration will be comprised between 5000 ppm to 15000 ppm. It goes without saying that the process works also with more catalyst. However the optimum concentration of metal will depend, as the person skilled in the art knows, on the nature of the latter, on the nature of the substrate, on the temperature and on the desired time of reaction.

According to any one of the above embodiments of the invention, the hydrogen source is a hydrocarbon comprising at least one secondary alcohol functional group and having a boiling point equal to or grater than 80° C., preferably equal to or greater than 110° C., even more preferably, equal to or greater than 120° C. Said hydrogen source borrows hydrogen while generating ketone. The borrowing hydrogen source may be a secondary alcohol. In particular, the borrowing hydrogen source may be of formula

wherein $R^4$ and $R^5$, independently from each other, represent a $C_{1-10}$ linear alkyl group optionally substituted by a hydroxy group or an aryl group, a $C_{2-10}$ linear alkenyl group optionally substituted by a hydroxy group or an aryl group, a $C_{3-10}$ branched or cyclic alkyl or alkenyl group optionally substituted by a hydroxy group or an aryl group, or a phenyl group optionally substituted by one to five $C_{1-3}$ alkyl or alkoxy groups, hydroxy groups or halogen atoms; or $R^4$ and $R^5$, when taken together, represent a $C_{2-10}$ linear or branched alkanediyl or alkenediyl optionally substituted by a hydroxy group or an aryl group. The hydrogen source of formula (V) is a $C_{4-10}$ compound.

The term "aryl group" designates the normal meaning in the art; i.e. an aromatic hydrocarbon group such as phenyl or naphthyl group optionally substituted. Non-limiting examples of the optional substituent of the aryl group may include $C_{1-3}$ alkyl or alkoxy group, a hydroxy group or a halogen atom.

According to any one of the above embodiments, $R^4$ may represent a $C_{1-10}$ linear alkyl group optionally substituted by a hydroxy group or an aryl group or a $C_{3-10}$ branched or cyclic alkyl group optionally substituted by a hydroxy group or an aryl group, or a phenyl group optionally substituted by one to five $C_{1-3}$ alkyl or alkoxy group, a hydroxy group or a halogen atom. Preferably, $R^4$ may represent a $C_{1-10}$ linear alkyl group optionally substituted by a hydroxy group or a $C_{3-10}$ branched or cyclic alkyl group optionally substituted by a hydroxy group. Preferably, $R^4$ may represent a $C_{3-8}$ linear or branched alkyl group optionally substituted by a hydroxy group. Even more preferably, $R^4$ may represent a methyl, ethyl, propyl, isopropyl, butyl, octyl group optionally substituted by a hydroxy group.

According to any one of the above embodiments, $R^5$ may represent a $C_{1-10}$ linear alkyl group optionally substituted by a hydroxy group or an aryl group or a $C_{3-10}$ branched or cyclic alkyl group optionally substituted by a hydroxy group or an aryl group. Preferably, $R^5$ may represent a methyl, an ethyl or a propyl group.

According to any one of the above embodiments, $R^4$ and $R^5$, when taken together, may represent a $C_{4-7}$ linear, branched alkanediyl or alkenediyl optionally substituted by a hydroxy group. Preferably, $R^4$ and $R^5$, when taken together, may represent a $C_{4-7}$ linear alkanediyl. Even more preferably, $R^4$ and $R^5$, when taken together, may represent a $C_{4-5}$ linear alkanediyl.

Non-limiting example of suitable hydrogen source may include 1-phenylethan-1-ol, 2-methyl-2,4-pentanediol, cyclohexanol, 4-methylpentan-2-ol, cyclopentanol or octan-2-ol. Preferably, the hydrogen source may be cyclopentanol, or 4-methylpentan-2-ol.

The hydrogen source can be added into the reaction medium of the invention's process in a large range of concentrations. As non-limiting examples, one can cite as hydrogen source concentration values those ranging from 1 equivalent to 50 equivalents, or even between 1 equivalent to 5 equivalents, relative to the amount of compound of formula (II). It goes without saying that the optimum concentration of hydrogen source will depend, as the person skilled in the art knows, on the nature of the latter, on the nature of the substrate, of the temperature and on the catalyst used during the process, as well as the desired time of reaction.

According to any embodiments of the invention, the invention process may be performed in the presence of a co-catalyst. Non-limiting examples of suitable co-catalyst include tertiary amine, such as pyridine, bis-pyridine, trimethylamine, lutidine, N,N-Diisopropylethylamine or 1,8-Diazabicyclo[5.4.0]undec-7-ene or tertiary phosphine, or phenols optionally substituted, or bis phenols optionally substituted. Preferably, the cocatalyst may be a tertiary amine or a pyridine or a substituted bis phenol. Even more preferably, the cocatalyst may be a methylpyridine or a dihydroxy biphenyl ingredient such as 2,2'-dihydroxydiphenylmethane, 2,2'-dihydroxybiphenyl.

The co-catalyst can be added into the reaction medium of the invention's process in a large range of concentrations. As non-limiting examples, one can cite as co-catalyst concentration values those ranging from 0.1 equivalent to 2 equivalent relative to the catalyst, It goes without saying that the optimum concentration of the co-catalyst will depend, as the person skilled in the art knows, on the nature of the latter, on the nature of the substrate, of the temperature and on the catalyst used during the process, as well as the desired time of reaction.

The invention's process is carried out under batch or continuous conditions.

The reaction can be carried out in the absence of a solvent.

The temperature of the invention's process may be comprised between 120° C. and 300° C., more preferably in the range comprised between 150° C. and 250° C. Of course, a person skilled in the art is also able to select the preferred temperature as a function of the melting and boiling point of the hydrogen source and of the starting and final products as well as the desired time of reaction or conversion.

The invention's process may be performed under atmospheric pressure or under a slight vacuum. The invention's process may be performed under inert atmosphere such as nitrogen or argon.

According to any one of the above embodiments of the invention, the more volatile compounds generated during the invention's process are removed continuously during the invention's process. The removal of said more volatile compounds such as water and ketone formed during the invention process may be distillated during the invention process.

EXAMPLES

The invention will now be described in further details by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Preparation of Compound of Formula (I) Starting from Compound of Formula (II)

In 1 l glass reactor equipped with a mechanical stirrer, a packed column, a reflux condenser, 250 g of 3-methyl-1,5-cyclopentadecanedione (0.99 mol), 50 g of the hydrogen source (see Table 1) and V(acac)$_3$ (17.2 g, 0.049 mol), were loaded at atmospheric pressure. The mixture was stirred and heated to reflux then the rest of the hydrogen source (450 g) was dosed over 22 h while distilling into a flask the light fraction that was formed during the reaction (water and resulting ketone). The resulting mixture was cooled to 100° C. and the remaining solvent was concentrated under vacuum. The residual oil (230 g) was flash distilled (170° C., 1 mbar) and the distillate was analyzed by GC (see Table 1).

TABLE 1

Preparation of compound of formula (I) from compound of formula (II)

| Hydrogen source | Amount of hydrogen source (g) | Reaction temperature (° C.) | Reaction pressure (mbar) | Compound (I) (%) | Compound (II) (%) | Yield (%)[2)] |
|---|---|---|---|---|---|---|
| 4-Methylpentan 2-ol[1)] | 500 | 170 | 1000 | 89.1 | 3 | 85.6 |
| Cyclopentanol[1)] | 500 | 175 | 1000 | 89.6 | 1 | 89.7 |

[1)]pre loading of 10% of the total charge then addition of the rest over 16 h.
[2)]mainly full conversion and high selectivity.

Example 2

Preparation of Compound of Formula (I) Starting from Compound of Formula (II)

In 1 l glass reactor equipped with a mechanical stirrer, a packed column, a reflux condenser, 250 g of 3-methyl-1,5-cyclopentadecanedione (0.99 mol), 50 g of cyclohexanol, Zr(OPr)$_4$ (4.63 g, 0.0098 mol, 70% in PrOH), and 2,2'-dihydroxydiphenylmethane (1.59 g, 0.0098 mol) were loaded at atmospheric pressure. The mixture was stirred and heated to reflux then the rest of the hydrogen source (450 g) was dosed over 22 h while distilling into a flask the light fraction that was formed during the reaction (water, cyclohexanol, cyclohexanone). The resulting mixture was cooled to 100° C. and the remaining solvent was concentrated under vacuum. The residual oil (242 g) was flash distilled (170° C., 1 mbar) and the distillate was analyzed by GC (compound I 92.7% purity, 91.2% yield). 3-methyl-1,5-cyclopentadecanediol was not formed and 3-methyl-1,5-cyclopentadecanedione was completely converted.

Example 3

Preparation of Compound of Formula (I) Starting from Compound of Formula (II)

In 1 l glass reactor equipped with a mechanical stirrer, a packed column, a reflux condenser, 250 g of 3-methyl-1,5-cyclopentadecanedione (0.99 mol), 50 g of 2-Octanol, Zr(OPr)$_4$ (9.26 g, 0.0196 mol, 70% in PrOH), and 2,2'-dihydroxybiphenyl (3.7 g, 0.0196 mol) were loaded at 200 mbar. The mixture was stirred and heated to reflux then the rest of the hydrogen source (250 g) was dosed over 16 h while distilling into a flask the light fraction that was formed during the reaction (water, 2-Octanol, 2-Octanone). The resulting mixture was cooled to 100° C. and the remaining solvent was concentrated under vacuum. The residual oil (230 g) was flash distilled (180° C., 1 mbar) and the distillate was analyzed by GC (compound I 89.2% purity, 94.1% yield). 3-methyl-1,5-cyclopentadecanediol was not formed and 3-methyl-1,5-cyclopentadecanedione was completely converted.

Example 4

Preparation of Compound of Formula (I) Starting from Compound of Formula (II)

In 1 l glass reactor equipped with a mechanical stirrer, a packed column, a reflux condenser, 250 g of 3-methyl-1,5-cyclopentadecanedione (0.99 mol), 50 g of the hydrogen source (see Table 2), Ti(OiPr)$_4$ (5.6 g, 0.02 mol), and 2,2'-dihydroxybiphenyl (3.7 g, 0.02 mol) were loaded at a pressure indicated in the table 2. The mixture was stirred and heated to reflux then the rest of the hydrogen source (450 g) was dosed over 22 h while distilling into a flask the light fraction that was formed during the reaction (water and resulting ketone). The resulting mixture was cooled to 100° C. and the remaining solvent was concentrated under vacuum. The residual oil (≈230 g) was flash distilled (170° C., 1 mbar) and the distillate was analyzed by GC (see Table 2).

TABLE 2

Preparation of compound of formula (I) from compound of formula (II)

| Hydrogen source | Amount of hydrogen source (g) | Reaction temperature (° C.) | Reaction pressure (mbar) | Compound (I) (%) | Compound (II) (%) | Yield (%) |
|---|---|---|---|---|---|---|
| 4-Methylpentan 2-ol[1] | 500 | 170 | 1000 | 88.5 | 1.35 | 95.6 |
| Cyclopentanol[1] | 500 | 175 | 1000 | 84.1 | 0.9 | 95.2 |
| Cyclohexanol[1] | 500 | 170 | 450 | 83.8 | 1.35 | 93 |

[1] pre loading of 10% of the total charge then addition of the rest over 16 h.
2) mainly full conversion and high selectivity.

Example 5

Preparation of Compound of Formula (I) Starting from Compound of Formula (II)

In 1 l glass reactor equipped with a mechanical stirrer, a packed column, a reflux condenser, 250 g of 3-methyl-1,5-cyclopentadecanedione (0.99 mol), 50 g of cyclopentanol, Al(OBu)$_3$ (12.3 g, 0.05 mol), and 2,2'-dihydroxydiphenylmethane (8 g, 0.05 mol) were loaded at atmospheric pressure. The mixture was stirred and heated to reflux then the rest of the hydrogen source (450 g) was dosed over 22 h while distilling into a flask the light fraction that was formed during the reaction (water, cyclopentanol, cyclopentanone). The resulting mixture was cooled to 100° C. and the remaining solvent was concentrated under vacuum. The residual oil (247 g) was flash distilled (170° C., 1 mbar) and the distillate was analyzed by GC (compound I 85% purity, 85% yield). 3-methyl-1,5-cyclopentadecanediol was not formed and 3-methyl-1,5-cyclopentadecanedione was completely converted.

The invention claimed is:

1. A process for the preparation of a compound of formula (I)

in a form of any one of its stereoisomers or a mixture thereof and wherein $R^1$ represents a linear or branched $C_{1-5}$ alkanediyl or alkenediyl group, optionally substituted by a phenyl group and $R^2$ represents a linear or branched $C_{1-10}$ alkanediyl or alkenediyl group, optionally substituted by a phenyl group;

comprising the reaction of a compound of the formula (II)

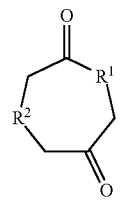

in a form of any one of its stereoisomers and wherein $R^1$ and $R^2$ have the same meaning as defined in formula (I);

with a metal catalyst, provided that ruthenium catalyst is excluded, and in the presence of a hydrogen source.

2. The process according to claim 1, characterized in that $R^1$ represents a linear or branched $C_{1-4}$ alkanediyl group.

3. The process according to claim 1, characterized in that $R^1$ represents a linear or branched $C_{2-3}$ alkanediyl group.

4. The process according to according to claim 1, characterized in that $R^1$ represents a 1,2-propanediyl group or 1,2-ethanediyl group.

5. The process according to claim 1, characterized in that $R^2$ represents a linear or branched $C_{4-9}$ alkanediyl group.

6. The process according to claim 1, characterized in that $R^2$ represents a linear or branched $C_{6-9}$ alkanediyl group.

7. The process according to claim 1, characterized in that $R^2$ represents a 1,8-octanediyl group.

8. The process according to claim 1, characterized in that compound of formula (I) is selected from the group consisting of 12-oxabicyclo[6.3.1]dodec-8-ene, 10-methyl-12-oxabicyclo[6.3.1]dodec-8-ene, 13-oxabicyclo[7.3.1]tridec- 9-ene, 11-methyl-13-oxabicyclo[7.3.1]tridec-9-ene, 14-oxabicyclo[8.3.1]tetradec-10-ene, 12-methyl-14-oxabicyclo[8.3.1]tetradec-10-ene, 15-oxabicyclo[9.3.1]pentadec-11-ene, 13-methyl-15-oxabicyclo[9.3.1]pentadec-11-ene, 16-oxabicyclo[10.3.1]hexadec-12-ene, 14-methyl-16-oxabicyclo[10.3.1]hexadec-12-ene, 17-oxabicyclo[11.3.1]heptadec-13-ene and 15-methyl-17-oxabicyclo[11.3.1]heptadec-13-ene.

9. The process according to claim 1, characterized in that compound of formula (II) is selected from the group consisting of cycloundecane-1,5-dione, 3-methylcycloundecane-1,5-dione, cyclododecane-1,5-dione, 3-methylcyclododecane-1,5-dione, cyclotridecane-1,5-dione, 3-methylcyclotridecane-1,5-dione, cyclotetradecane-1,5-dione, 3-methylcyclotetradecane-1,5-dione, cyclopentadecane-1,5-dione, 3-methylcyclopentadecane-1,5-dione, cyclohexadecane-1,5-dione and 3-methylcyclohexadecane-1,5-dione.

10. The process according to claim 1, characterized in that the metal catalyst is of formula

[M(O)m(X)n]    (IV)

wherein M is a metal selected from the group consisting of transition metal or post transition metal, m is 0 or 1 or 2, X represents an anionic ligand; and n is an integer between 1 to 6.

11. The process according to claim 10, characterized in that M is selected from the group consisting of Aluminum, Titanium, Zirconium and Vanadium.

12. The process according to claim 1, characterized in that the metal catalyst is selected from the group consisting of [Al(OR)$_3$], [Al(OAc)$_3$], [Al(acac)$_3$], [Ti(OR)$_4$], [Ti(O)(acac)$_2$], [Zr(OR)$_4$], [Zr(acac)$_4$], [V(O)(acac)$_2$], [V(acac)$_3$] and [V(O)(OR)$_3$]; R being a $C_{1-6}$ alkyl group.

13. The process according to claim 1, characterized in that the hydrogen source is a hydrocarbon comprising at least one secondary alcohol functional group and having a boiling point equal or greater than 80° C.

14. The process according to claim 1, characterized in that the hydrogen source is of formula

(V)

wherein $R^4$ and $R^5$, independently from each other, represent a $C_{1-10}$ linear alkyl group optionally substituted by a hydroxy group or an aryl group, a $C_{2-10}$ linear alkenyl group optionally substituted by a hydroxy group or an aryl group, a $C_{3-10}$ branched or cyclic alkyl or alkenyl group optionally substituted by a hydroxy group or an aryl group, or a phenyl group optionally substituted by one to five $C_{1-3}$ alkyl or alkoxy groups, hydroxy groups or halogen atoms; or $R^4$ and $R^5$, when taken together, represent a $C_{2-10}$ linear or branched alkanediyl or alkenediyl optionally substituted by a hydroxy group or an aryl group.

15. The process according to claim 1, characterized in that the hydrogen source is 1-phenylethan-1-ol, 2-methyl-2,4-pentanediol, cyclohexanol, 4-methylpentan-2-ol, cyclopentanol or octan-2-ol.

* * * * *